United States Patent
Kim et al.

(10) Patent No.: US 9,788,903 B2
(45) Date of Patent: Oct. 17, 2017

(54) HYBRID CONTROL SURGICAL ROBOTIC SYSTEM

(71) Applicant: Children's National Medical Center, Washington, DC (US)

(72) Inventors: Peter C. W. Kim, Washington, DC (US); Yonjae Kim, Falls Church, VA (US); Peng Cheng, Fairfax, VA (US); Axel Krieger, Alexandria, VA (US); Justin Opfermann, Silver Spring, MD (US); Ryan Decker, Baltimore, MD (US)

(73) Assignee: Children's National Medical Center, Washington, DC (US)

( * ) Notice: Subject to any disclaimer, the term of this patent is extended or adjusted under 35 U.S.C. 154(b) by 720 days.

(21) Appl. No.: 14/172,502

(22) Filed: Feb. 4, 2014

(65) Prior Publication Data
US 2014/0222023 A1  Aug. 7, 2014

Related U.S. Application Data

(60) Provisional application No. 61/760,378, filed on Feb. 4, 2013.

(51) Int. Cl.
*A61B 19/00* (2006.01)
*A61B 34/30* (2016.01)
(Continued)

(52) U.S. Cl.
CPC .......... *A61B 19/2203* (2013.01); *A61B 34/30* (2016.02); *A61B 34/76* (2016.02);
(Continued)

(58) Field of Classification Search
None
See application file for complete search history.

(56) References Cited

U.S. PATENT DOCUMENTS

| 5,397,323 A | 3/1995 | Taylor et al. |
| 5,649,956 A | 7/1997 | Jensen et al. |

(Continued)

FOREIGN PATENT DOCUMENTS

| CN | 101443162 A | 5/2009 |
| EP | 0 774 329 A1 | 5/1997 |

(Continued)

OTHER PUBLICATIONS

International Search Report and Written Opinion issued Aug. 15, 2014 in PCT/US14/14626.

(Continued)

*Primary Examiner* — Brian T Gedeon
(74) *Attorney, Agent, or Firm* — Oblon, McClelland, Maier & Neustadt, L.L.P.

(57) ABSTRACT

The present disclosure describes a method and system for performing robot-assisted surgical procedures. The system includes a robotic arm system assembly, an end effector assembly, and a hybrid control mechanism for robotic surgery. The robotic arm is a lightweight, bedside robot with a large range of motion, which can be easily manipulated to position endoscope and surgical instruments. The control console is mounted at the distal end of the robotic arm to enable robotic arm to follow operators arm movement, provide physical support, filter out hand tremor, and constrain motion. A universal adapter is also described as an interface to connect traditional laparoscopic tools to the robotic arm.

19 Claims, 13 Drawing Sheets

(51) Int. Cl.
*A61B 34/00* (2016.01)
*A61B 18/14* (2006.01)
*A61B 17/00* (2006.01)
*A61B 90/00* (2016.01)
*A61B 34/20* (2016.01)

(52) U.S. Cl.
CPC ..... *A61B 18/14* (2013.01); *A61B 2017/00477* (2013.01); *A61B 2017/00486* (2013.01); *A61B 2034/2059* (2016.02); *A61B 2090/064* (2016.02)

(56) References Cited

U.S. PATENT DOCUMENTS

| | | | |
|---|---|---|---|
| 5,954,692 | A | 9/1999 | Smith et al. |
| 6,239,784 | B1 | 5/2001 | Holmes |
| 6,413,229 | B1 | 7/2002 | Kramer et al. |
| 7,747,311 | B2 | 6/2010 | Quaid, III |
| 7,813,784 | B2 | 10/2010 | Marquart et al. |
| 8,188,843 | B2 | 5/2012 | Helmer et al. |
| 8,332,072 | B1 | 12/2012 | Schaible et al. |
| 2007/0250078 | A1 | 10/2007 | Stuart |
| 2008/0009771 | A1 | 1/2008 | Perry et al. |
| 2009/0030449 | A1 | 1/2009 | Kawai et al. |
| 2009/0240259 | A1 | 9/2009 | Nelson et al. |
| 2010/0016855 | A1 | 1/2010 | Ramstein et al. |
| 2010/0331855 | A1 | 12/2010 | Zhao et al. |
| 2012/0130399 | A1 | 5/2012 | Moll et al. |
| 2012/0199633 | A1 | 8/2012 | Shelton, IV et al. |
| 2012/0283747 | A1 | 11/2012 | Popovic |
| 2013/0211196 | A1 | 8/2013 | Belson et al. |
| 2014/0005684 | A1 | 1/2014 | Kim et al. |

FOREIGN PATENT DOCUMENTS

| | | |
|---|---|---|
| EP | 1 486 178 A1 | 12/2004 |
| EP | 1 815 950 A1 | 8/2007 |
| EP | 1 979 136 B1 | 5/2011 |
| WO | WO 2011/002215 A2 | 1/2011 |
| WO | WO 2011/058530 A1 | 5/2011 |
| WO | WO 2012/012565 A2 | 1/2012 |
| WO | WO 2012/018816 A2 | 2/2012 |
| WO | WO 2012/018823 A2 | 2/2012 |
| WO | WO 2013/026412 A1 | 2/2013 |

OTHER PUBLICATIONS

Combined Chinese Office Action and Search Report issued Dec. 20, 2016 in patent application No. 201480007291.5 with partial English translation.

Partial Supplementary European Search Report issued on Oct. 28, 2016 in Patent Application No. 14746186.7.

HYBRID CONTROL SURGICAL ROBOTIC SYSTEM

BACKGROUND OF THE INVENTION

Field of Invention

The present disclosure is related to the field of robot-assisted surgery.

Description of the Related Art

Robotic surgical systems are useful in minimally invasive surgery by enhancing the vision and dexterity of the surgeon. The Da Vinci from Intuitive Surgical is the only commercial robot for soft-tissue surgery on the market today. The Da Vinci system has advanced the field of surgery by providing a less invasive alternative to open procedures (i.e. prostatectomy or hysterectomy) by enabling the surgeon to access and manipulate in difficult to reach anatomical regions, such as deep in the pelvis or the retroperitoneum. Today, over 90% of Da Vinci cases are genitourinary procedures performed in the in the pelvic cavity, such as prostatectomy, hysterectomy, cystectomy, pyeloplasty, sacrocolpopexy, myomectomy, and endometriosis resection. In 2011, there were 360,000 procedures done with the Da Vinci system, among which prostatectomy and hysterectomy account for 75% of these procedures [Intuitive Surgical Inc. Annual Report 2012].

Da Vinci's key value proposition is that it enables Urologist/Gynecologist to access hard to reach deep and tight pelvic spaces in order to perform laparoscopic surgeries with enhanced 3D visualization and improved dexterity, which would otherwise be technically very challenging using a traditional laparoscopic approach. It is best suited for operation in a relatively small field and for precision dissection in a confined volume, but it is not suitable for larger interventions, such as mobilization of the colon, because these types of procedures usually require wide ranges of motion. Previous studies showed that intuitive controls of robotic systems are more comparable to the motions performed by a surgeon during open surgery and can shorten the procedure learning curve, even in the hands of relatively inexperienced laparoscopic surgeons. Ahlering et al. demonstrated a similar finding in urological surgery, where a robotic interface allowed a surgeon with limited laparoscopic familiarity to perform minimally invasive radical prostatectomy, with results comparable to those of an experienced laparoscopic surgeon, after completing only twelve cases [Ahlering, et al. J Urol 2003].

Despite the utility of Da Vinci in pelvic surgeries, the technology in its current form is not suited for general surgery, especially colorectal resection during which multiple quadrants of the abdomen are traversed and the surgeon must often adjust or tilt the patient and operating table to achieve better access to target tissues. In order to effectively use robotics in procedures such as this, physicians would need to greatly modify their technique or dock and undock the robot in the middle of the procedure, which can significantly increase operating times and possibly increase the risk of harming the patient. For instance, a total robotically performed sigmoid colectomy requires undocking the robot from the upper abdominal ports, repositioning the patient, moving the robot and re-docking to the lower abdominal ports. An action that usually takes a couple of seconds in conventional laparoscopy has become a cumbersome 10 minute or more exercise performed by specialized assistants.

A further shortcoming of current robotic systems is their large footprint on both master and slave sides, which can impede access to the patient lying on the operating table, and also poses a significant challenge for proper patient positioning and port placement. Even small deviations in port placement could result in collision of the robotic arms or failure to reach the intended target area. It also lacks haptic feedback (tactile and force feedback), making it unsuitable for surgical anastomosis as these require water-tight and tension-free suturing to mitigate the chance of anastomosis breakdown post-operatively. According to our survey of surgeons, there is very limited application for Da Vinci in colorectal surgery, even with its recently approved Endo Wrist Stapler. There might be a very small niche for it, such as lower anterior rectal resection deep in the pelvis and anastomosis can be accomplished by using a trans-anal circular stapler.

Traditional minimally invasive colorectal surgeries include the following stages: (1) Careful dissection to provide adequate hemostasis and obtain access to the target tissue; (2) Repair (as in treatment of a perforation) or bypass/removal of a lesion (as in colorectal cancer); (3) Anastomosis of the remaining ends of bowel; (4) Irrigation of the abdominal and pelvic cavities if indicated; and (5) Appropriate closure of the fascia and skin. Each of these basic stages has very different design requirements when utilizing a robotic system. In the exploration stage, the ideal system would provide a wide range of motion for identifying the target tissue and for optimal use of surgical tools. The second and third stages typically require a long operating time, and put a great amount of physical strain on the surgeon. A system that enhances surgeon's dexterity as well as providing arm support is needed.

In summary, current robotic system enable the surgeons in some disciplines to perform MIS (Minimally Invasive Surgery) procedures otherwise difficult to do. However, a more flexible, modular, intelligent robotic functionality is needed to facilitate the use of robotically assisted MIS in the general surgery field. There is a clear clinical need for a system that not only lowers the technical barriers for performing MIS procedures, but also improves surgical outcome and efficiency.

Several previous patents describe devices meant to aid the surgeon by constraining motions and providing support. U.S. Pat. No. 5,397,323, entitled "Remote center-of-motion robot for surgery," and U.S. Publication 2009/0240259, entitled "System and methods for controlling surgical tool elements," both describe systems that would limit the movement of a tool with a remote degree of freedom and allow for robotic master-slave control.

U.S. Publication 2007/0250078, entitled "Surgical manipulator," describes a device that can position a surgical tool and provide haptic feedback.

U.S. Publication 2012/0283747, entitled "Human-robot shared control for endoscopic assistant robot," describes a robotic-arm positioning system that can support an endoscope that can be operated with preloaded procedures or manually with varying stiffness.

U.S. Pat. No. 6,239,784, entitled "Exo-skeletal haptic computer human/computer interface device," describes a hand-mounted exoskeleton glove-like haptic interface that can be used to interact with computers.

U.S. Pat. No. 6,413,229, entitled "Force-feedback interface device for the hand," describes a similar haptic glove-like interface that can be mounted in different ways and be used to manipulate both virtual and physical objects.

U.S. Pat. No. 5,954,692, entitled "Endoscopic robotic surgical tools and methods," describes a wearable encoder/robotic interface that allows direct control of surgical instruments.

U.S. Pat. No. 8,188,843, entitled "Haptic device gravity compensation," describes a haptic input device with gravity compensation.

U.S. Pat. No. 8,332,072, entitled "Robotic Hand Controller," describes a robotic hand controller with 8 degrees of freedom with force feedback.

U.S. Publication 2008/0009771, entitled "Exosceleton," describes a wearable structure with links and joints corresponding to the human body. Transducers on the structure allow for exchange of motion and information between structure and user, and enable control of movement of the structure.

EP 0774329A, entitled "Telerobotic laparoscopic manipulator," describes a manipulatable hand for use in laparoscopic surgery having a controlled hand remote from the operator, and having at least one controlled finger.

U.S. Pat. No. 7,813,784, entitled "Interactive computer-assisted surgery system and method," describes a method and system for providing computer assistance for performing a medical procedure.

U.S. Pat. No. 7,747,311, entitled "System and method for interactive haptic positioning of a medical device," describes a combination of a haptic device and a computer-assisted system for interactive haptic positioning. The entire disclosure of each of the above references is hereby incorporated by reference into this specification.

However, none of the above references involve utilizing features of the present disclosure to perform robot-assisted surgery with the robotic arm and end-effector tethered to the operator's arm. None have described a control console positioned on the robotic arm nor a universal adapter that mechanizes endoscopic tools. Furthermore, none of the above references describe a system that allows easy exchange between the different operation modes: manual, master-slave, and autonomous.

BRIEF SUMMARY OF THE INVENTION

As outlined above, there is need for a flexible and modular system in order to integrate robotic-assistive system into standard surgical practice. The present disclosure addresses the workflow and ergonomic challenges of the existing robotic surgery system by incorporating intelligent robots as an exoskeleton extension of surgeon's arm/hand. With the surgeon, robot, and control console integrated together in the surgical field, the surgeon may be provided with more control and awareness of the operating environment, may be able to perform procedures following a nature workflow, may encounter enhanced visualization, accuracy, and dexterity by using robotic tools, may experience less physical strain, and may improve the efficiency and safety of surgery by automating tasks with robotic assistance.

The workspace of the present disclosure is easily adjustable to accommodate surgeries that require large work areas, but its movement can also be constrained on command as needed (e.g. remote center of motion, "wrist" motion only, axial constraints). When prompted by the surgeon, the robot may take advantage of sensors in the system to autonomously perform various surgical tasks that would benefit from increased dexterity and speed, such as anastomosis. At the surgeon's discretion, the automated procedure may be stopped, at which point the surgeon may take over by manipulating the robot using master-slave control.

In manual/master-slave mode of operation, the surgeon may utilize a controller that either mimics the handle of a traditional laparoscopic tool or may utilize a glove-like interface that links the movements of the hand to the tool. The controller may be at bedside or be attached to the robot itself, and using various feedback and control techniques such as haptic feedback and gravity compensation, the robot/controller may reproduce the feel of performing a manual laparoscopic surgery. The robot may also enhance manual control of the tool by supporting the weight of the instrument and the surgeon's arm, removing tremors, providing strict motion constraints, etc. The surgeon is able to quickly switch between this manual mode and the previously describe automated mode in order to improve surgical performance.

The features of the present disclosure may allow the surgeon to improve surgical performance by utilizing optimized, automated robotic surgical procedures when appropriate, and by switching quickly to a master-slave control that enhances the surgeon's manual capabilities when necessary. The disclosed embodiments of the device may include a robotic arm with exchangeable tools that the robot interfaces through a universal adapter. The tool may be a standard laparoscopic tool, a modified/motorized tool, and/or a highly specialized tool meant for specific procedures. For interfacing a traditional laparoscopic tool, the robot may come with an attachment that utilizes the universal adapter and is able to produce the motions needed to actuate most laparoscopic tools (e.g. gripping the handle).

DESCRIPTION OF THE DRAWINGS

The characteristics and advantages of exemplary embodiments are set out in more detail in the following description, made with reference to the accompanying drawings.

DETAILED DESCRIPTION

Objects, advantages, and features of the exemplary hybrid control surgical robotic system described herein with be apparent to one skilled in the art from a consideration of this specification, including the attached drawings.

Figure 1:
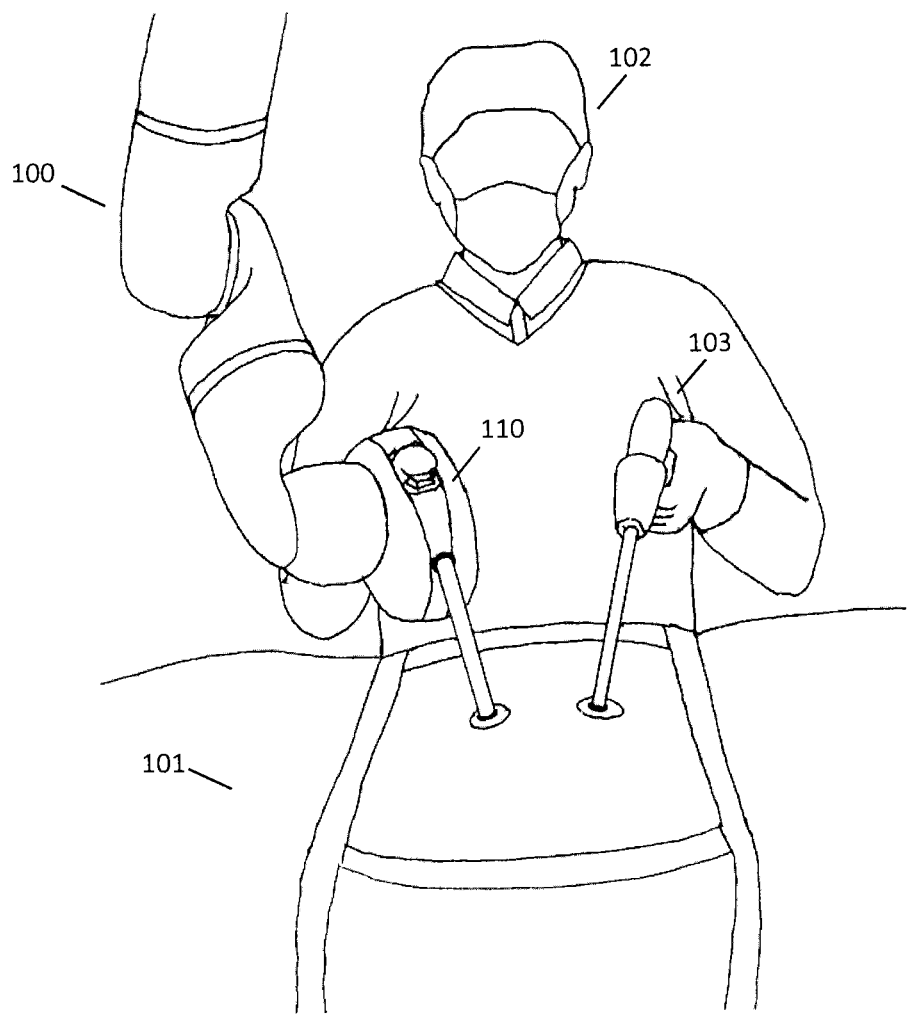
FIG. 1 shows an example of a surgical area setup where a surgeon may perform collaborative surgery using a universal tool adapter for hybrid techniques.

FIG. 1 represents one exemplary surgical area setup. In one embodiment, a robot (100) may be mounted near the operating bed (101), so that the surgeon (102) may switch between manual operation and robotic operation without leaving the bedside. The surgeon may use the robot (100) with one hand via a universal tool adapter (110), and a manual tool (103) in the other, or he may use two or more robots. In one embodiment, the manual tool (103) may be a laparoscopic tool.

Figure 2:
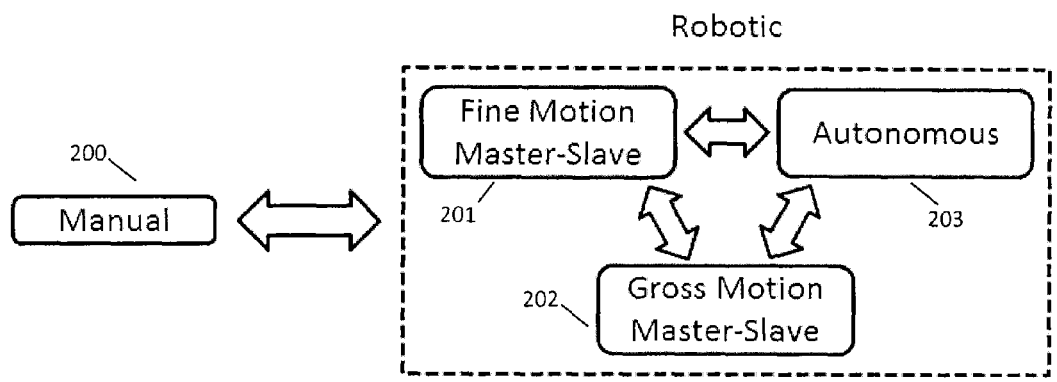
FIG. 2 shows examples of available modes of operations.

In one embodiment, FIG. 2 shows exemplary modes of operation available when utilizing this system: manual (200), fine motion master-slave (201), gross motion master-slave (202), and autonomous (203). The surgeon may opt to utilize any one of these modes and may switch between them as appropriate.

Figure 3:
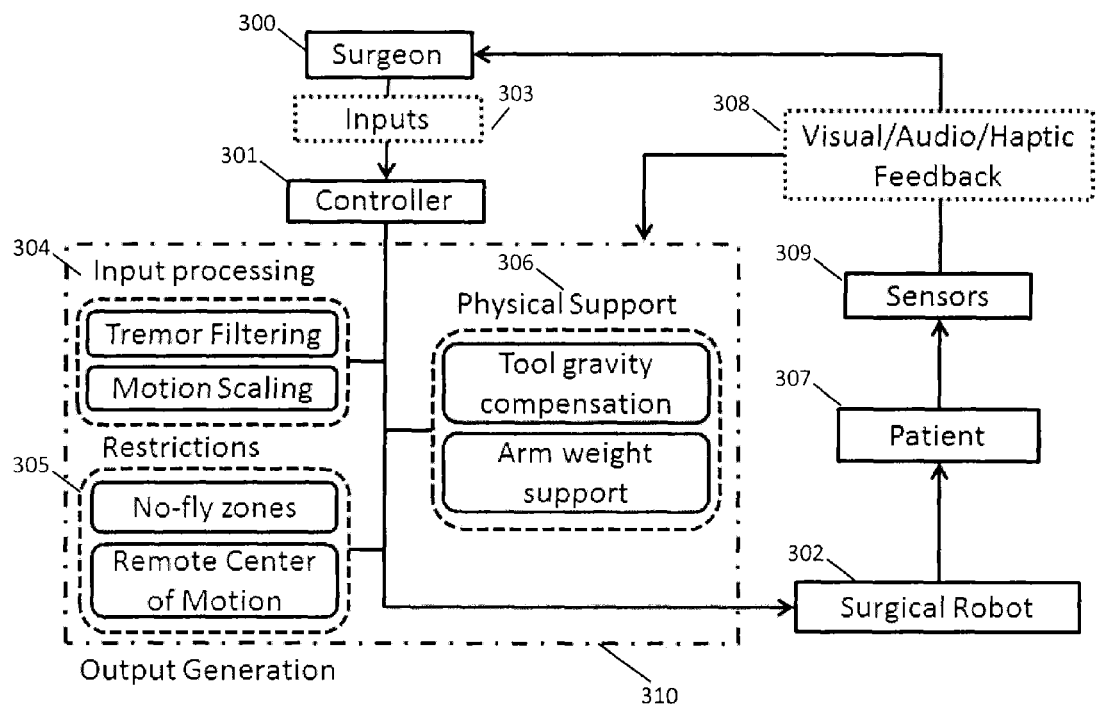
FIG. 3 shows an example of a general workflow for a master-slave mode of operation.

In one embodiment, a general workflow for fine and gross master-slave mode of operation is shown in FIG. 3. In this mode, the surgeon (300) may interact with the controller (301) to control the surgical robot (302). The surgeon's inputs (303) into the controller may then be processed via a control unit (310), a robot processor and/or a computer to generate an output for the robot, including: input processing (304) (e.g. tremor filtering, motion scaling), physical support (305) (e.g. tool gravity compensation, arm weight support), and movement restrictions (306) (e.g. no-fly zones, remote center of motion). The set of processing methods to apply may be customized to each surgeon, or may be changed on the fly. For example, if the surgeon would like to move the robot from one minimally invasive surgery port to another, the surgeon would pull out the robot with the current remote center of motion restriction in place. Once the robot is removed, the surgeon would remove the constraint before moving it to the other port, and then impose a new remote center of motion constrain on the robot. As the surgeon uses the robot to perform surgery on the patient (307), both the surgeon and the robot may receive sensory feedback (308) through one or more sensors (309).

In one embodiment, the control unit (310) may process input and/or operating conditions of at least one robot arm of the surgical robot (302) in order to operate the at least one robot arm. The control unit (310) may execute commands to the at least one robot arm to share a workspace and surgical elements, which will be described further below. The surgical elements may include at least one of a manual surgical tool, a robotic surgical tool, an electrocautery tool, and a display of the workspace. In one embodiment, the surgeon's inputs (303), or surgeon interaction inputs, may be detected via sensors of the at least one robot arm of the surgical robot (302) and/or an input controller. The sensors may include a force sensor and/or a position sensor coupled to the at least one robot arm and may be used to detect a surgeon's input. Based on surgeon interaction inputs, the surgical robot (302) may operate on a fully automated mode or a partially automated mode. In one embodiment, automated operation during the fully automated mode or partially automated mode may be interrupted or adjusted due to subsequent surgeon interaction inputs. In one embodiment, the control unit (310) may include a central processing unit (CPU) and/or circuitry to execute commands to operate the robot based on received inputs from one or more of sensors, surgeon interaction inputs, and an operating program of the surgical robot (302).

Figure 4A:
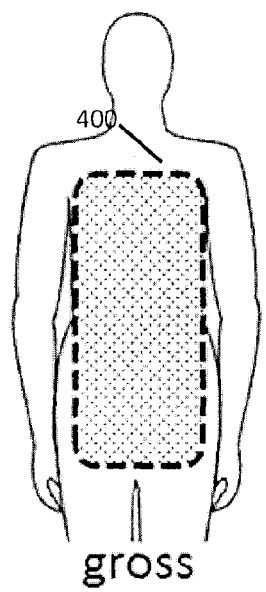
FIGS. 4A-4C show exemplary sets of constraints for a master-slave mode of operation.
Figure 4B:
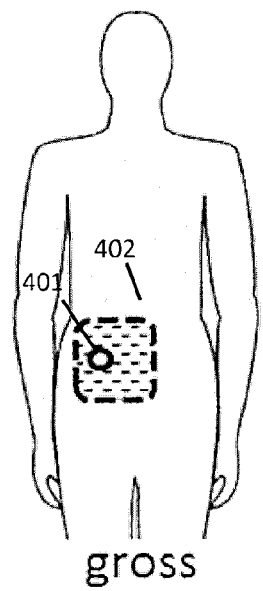
Figure 4C:
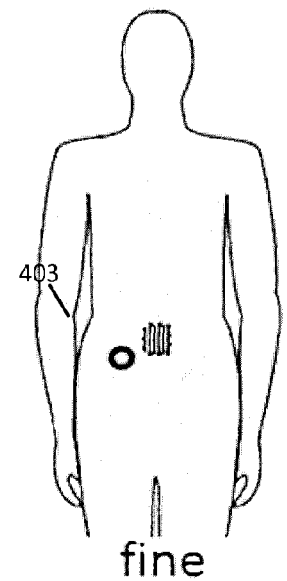

FIGS. 4A-4C show example sets of motion constraints in master-slave mode. FIG. 4A shows gross-motion mode without any constraints, which may allow the robot to move to any location in the surgical area (400). Once a port has been established in the patient, the robot may move to another set of constraints shown in FIG. 4B, which may include a remote center of motion (401) and a safe-working boundary (402). If necessary, the surgeon can opt to switch to using the fine-motor control, which further constrains (403) the motion of the robot as shown in FIG. 4C.

Figure 5:
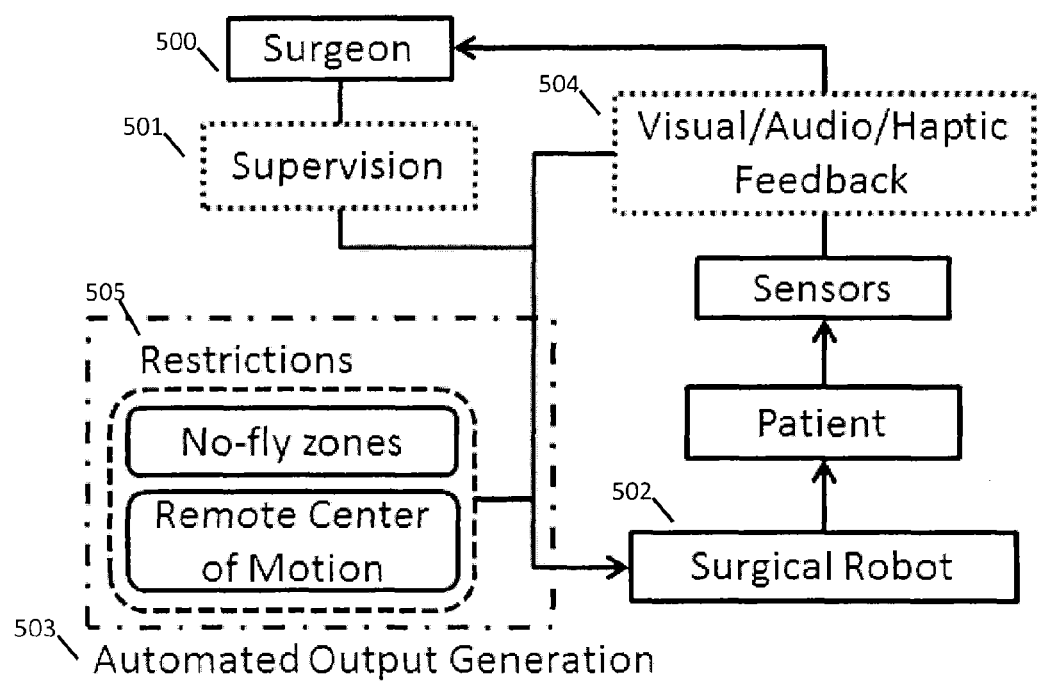
FIG. 5 shows an example of a general workflow for autonomous mode of operation.

In one embodiment, as shown in FIG. 5, an example of a general workflow for the supervised autonomous mode of operation is provided. In this mode, the surgeon (500) may supervise (501) the robot (502) as the robot motions are automatically generated (503) based on sensory information (504) and restrictions (505) in order to autonomously perform a surgical procedure.

In one embodiment, the surgeon may begin surgery without the robot in manual mode, using manual surgical tools to perform the tasks that he can. Once the surgeon becomes fatigued or reaches a point where use of the robot would be more effective, he may bring the robot into the surgical field using the gross motion master-slave control mode. From here, the robot can be switched between gross and fine motion control, depending on the situation. If the surgeon needs to perform an operation that requires high dexterity in a small work area, then he may employ the fine motor control. If the surgeon needs to make large motions, or needs to move to another work area, then he may employ the gross motor control. If the robot is programmed to do so, the surgeon may also set the robot to perform autonomous tasks, especially those tasks that require high dexterity and repetition such as anastomoses. At any time during the autonomous routine, the surgeon may interrupt the robot and take over in one of the two master-slave control configurations. Once the surgeon determines that the robot is no longer needed, he may pull the robot away from the surgical field and return to operating manually.

Figure 6:
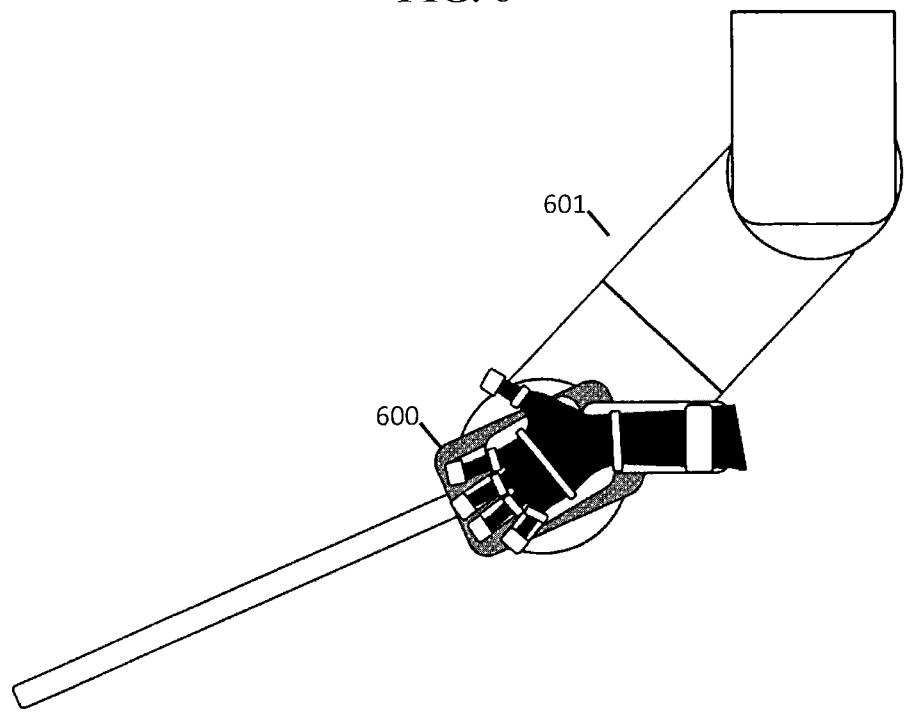
FIG. 6 shows an exemplary embodiment where the controller is attached to a robot.
Figure 7:
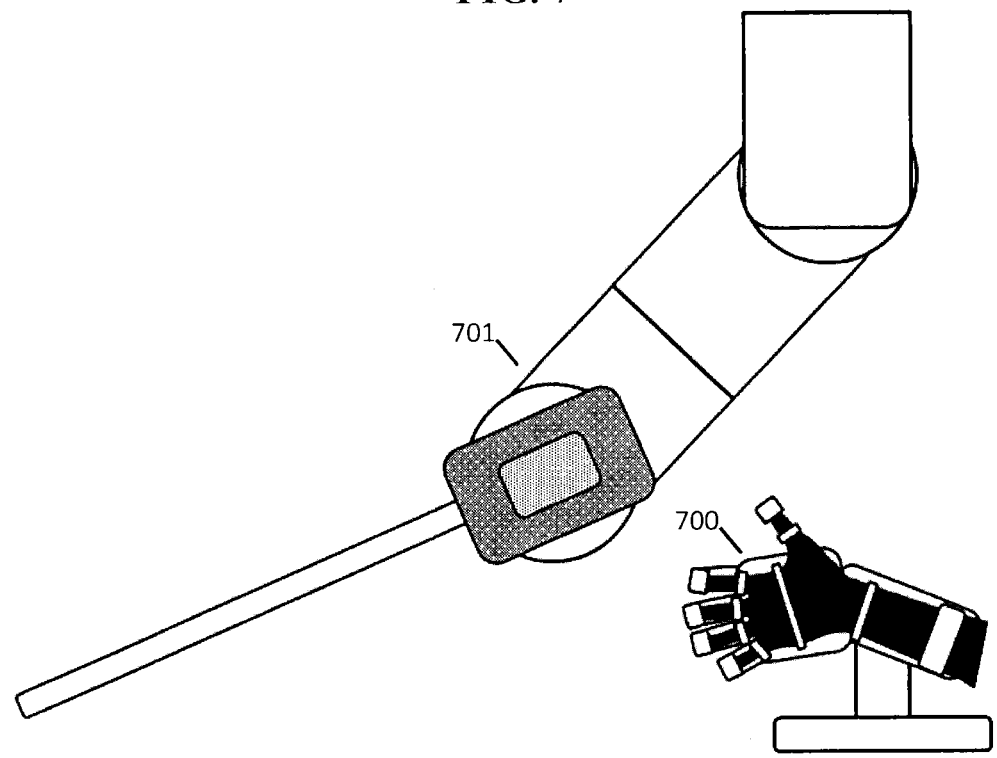
FIG. 7 shows an exemplary embodiment where the controller is detached from a robot.
Figure 8:
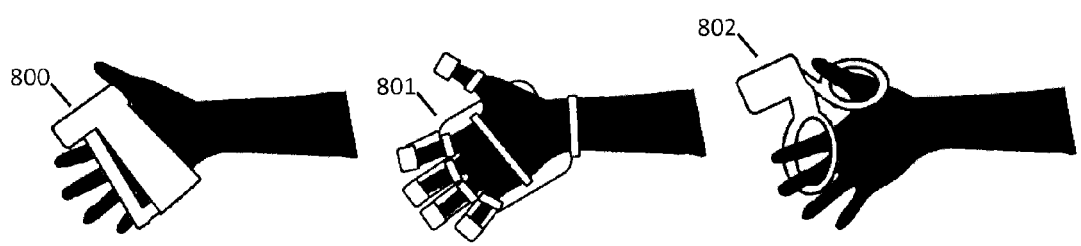
FIG. 8 shows exemplary controller shapes.

In one embodiment, the surgeon may interface with the robot through a controller that allows him to control the base robot's motions, the tool's orientation, and any degrees of freedom the tool may have. FIG. 6 shows an embodiment of the system where the master-slave controller (600) is attached to the robot (601), allowing the surgeon to feel that he is directly controlling the tools with the robot acting as a support. FIG. 7 shows an embodiment of the system where the master-slave controller (700) is detached from the robot (701), allowing the surgeon to control the robot more ergonomically and allowing for motion scaling between the controller and the robot output. In another embodiment, the surgeon may attach and detach the controller through the course of the surgery (e.g. attached for gross-motion master-slave control and detached for fine-motion master-slave control). FIG. 8 shows examples of controller shapes that can be used to control a wide range of tools. The controller shapes may include: a grip lever (800), a wearable glove controller (801), and a tool handle (802). In one embodiment, a controller may be detachably attached to an end of the robot, as shown in FIG. 6. In one embodiment, the controller is configured to quickly attach to or detach from the end of the robot.

In one embodiment, a kinematic model of a surgeon's arm may be produced. An arm pose may also be produced based on the robot end-effector's position in view of the kinematic model. The kinematic model and the arm pose may be provided to a robotic surgical system to determine an amount of gravity compensation required for the surgeon's arm at different work locations. The amount of gravity compensation, in the form of a dynamic force from the robot, applied against the surgeon's arm may be sufficient to support the arm to reduce fatigue. In one embodiment, the gravity compensation may enable the robot to assert a counter force against the surgeon's arm such that the arm feels substantially weightless without hindering the surgeon's intended movements. In one embodiment, the gravity compensation may enable the robot to assert a counter force against the surgeon's arm and/or attached surgical tool. The forces applied by the surgeon's arm or the attached surgical tool may include at least gravitational forces asserted by the arm or tool, respectively.

Figure 9A:
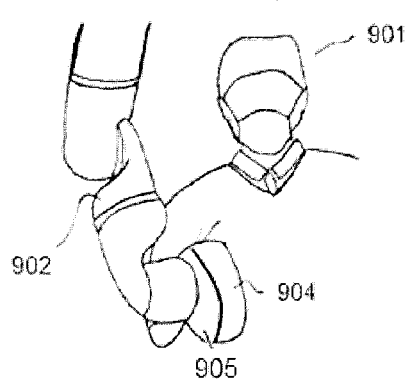
FIGS. 9A and 9B show examples of a robotic support for a surgeon.
Figure 9B:
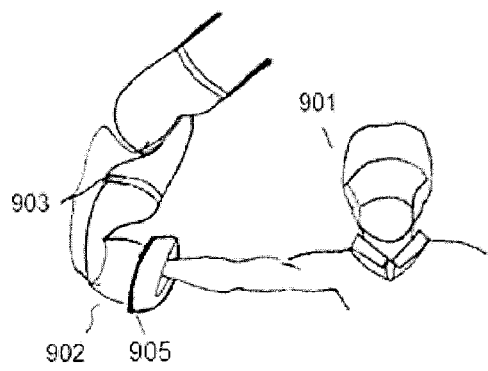

In one embodiment, as shown in FIGS. 9A and 9B, a surgeon (901) with his arm attached to a 6 degrees of freedom robot arm (902) using their hand, wrist, or forearm. To begin calibration, a surgeon may move their arm between at least two positions and the robot records these positions with one or more encoded joints (903) of the robot arm (902). A force sensor (905) may be provided within or on the robot arm (902) to detect a force applied by the arm of the surgeon (901) as it moves between the at least two positions. In one embodiment, the surgeon may calibrate the robot by moving their arm within an area defining a workspace of the surgeon. In one embodiment, the surgeon may signal to the robot when a boundary or an edge of the workspace has been reached. The surgeon may, for example, signal to the robot by issuing a voice command, depressing a button, toggling a switch, perform a predefined hand or arm gesture, depressing a foot pedal, etc. This signaling will define a virtual boundary for the robot in robot space.

After this calibration, the robot may compute and define a kinematic model of the surgeon arm. Subsequently, the robot end-effector (904) position may be translated into the arm pose. The arm pose will inform a gravity compensation mode where the surgeons arm will be supported at one or more locations by an amount of force which is appropriate for that arm pose. For example, an extended arm requires more support than an arm held close to the chest. In one embodiment, the one or more support locations may include the wrist, forearm, elbow, shoulder, or others.

In one embodiment, the robot may include a control unit, which may include a processor, main memory, and random access memory for storing and executing operating modes, and for defining and storing calibration parameters. For example, after calibration and other parameter definitions, the robot would not need to be recalibrated for a particular surgeon and operation.

FIGS. 10A-10F show tasks which involve the collaboration between the robot and surgeon. For example, collaborative procedures may include defining no-fly zones, tissue grasping, tissue cutting, tissue dissection, tissue joining, and/or tissue retraction. In one embodiment, an operator or surgeon may provide inputs, instructions, or commands to the robot by moving their hand, wrist, or forearm. In one embodiment, the robot may detect movements or force of the operator or surgeon via force and/or position sensors of the robot arm. In one embodiment, the operator or surgeon input may be in the form of a surgeon interaction input via a controller. In one embodiment, the control unit may execute a command to provide haptic feedback in response to the surgeon interaction input from the controller and/or in response to an input or operating condition detected by at least one sensor of the robot.

Figure 10A:
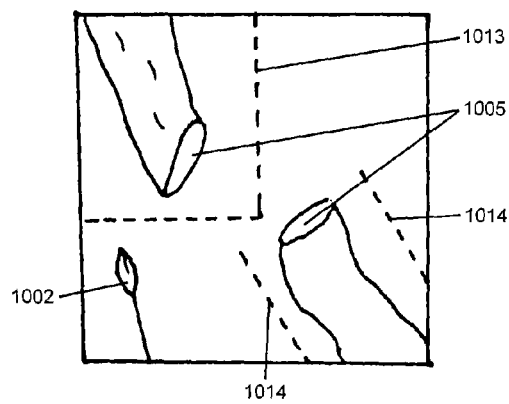
FIGS. 10A and 10B an example of collaborative actions between a robot and a surgeon where a surgeon may define a volumetric no-fly zone and/or a task-specific no-fly zone.
Figure 10B:
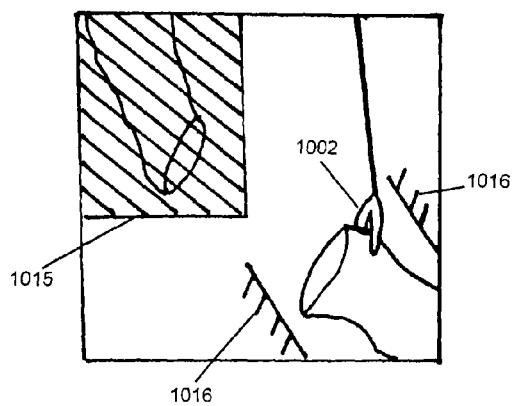

In one embodiment as shown in FIGS. 10A and 10B, a surgeon may define a volumetric no-fly zone (1015) and/or a task-specific no-fly zone (1016). As shown in FIGS. 10A and 10B, the tissue (1005) is in two segments, and a boundary (1013) is drawn by tracing a surgeon's tool (1002) on or around a surgical area, or by signaling to the robot, to define a general volumetric no-fly zone (1015). This volumetric no-fly zone (1015) may be enforced by the robot to prevent the tool (1002) from entering the region. The surgeon's tool (1002) may define edges (1014) of a task-specific no-fly zone (1016) by tracing or by signaling to the robot. The task-specific no-fly zone (1016) may be enforced by the robot during operation. In one embodiment as shown in FIGS. 10A and 10B, a task-specific no-fly zone (1016) may be enforced during a tissue grasping procedure. In one embodiment, a controller may be directly or indirectly connected to the tool (1002). The controller may receive surgeon interaction inputs, including tracing performed via the tool (1002) or signaling, which may be used to define the no-fly zones. In one embodiment, the task-specific no-fly zone (1016) may include abstract geometries, including planes. In one embodiment, the task-specific zone (1016) may dynamically change according to a detected surgical scene or task performed by the robot or the surgeon.

In one embodiment, a workspace display may be provided to depict the edges, boundaries (1013), and other virtual inputs (1014) as they are selected. In one embodiment, the workspace display may depict the general volumetric no-fly zone (1015) and/or the task-specific no-fly zone (1016) once the boundary (1013) and/or edges (1014) selection process has been completed. In one embodiment, the workspace display may be connected with the controller of the robot, and the controller may save and recall the volumetric no-fly zone (1015) and/or a task-specific no-fly zone (1016) when executing various operating modes.

Figure 10C:
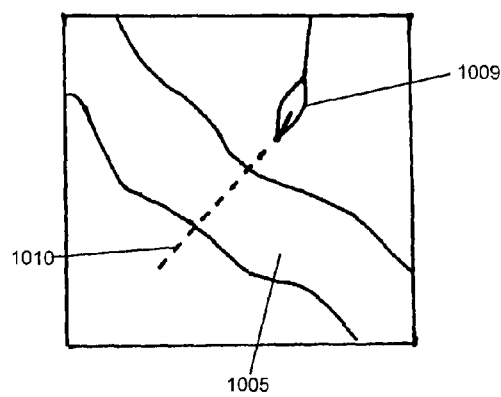
FIGS. 10C and 10D show an example of collaborative actions between a robot and a surgeon where a surgeon may define a planned incision line.
Figure 10D:
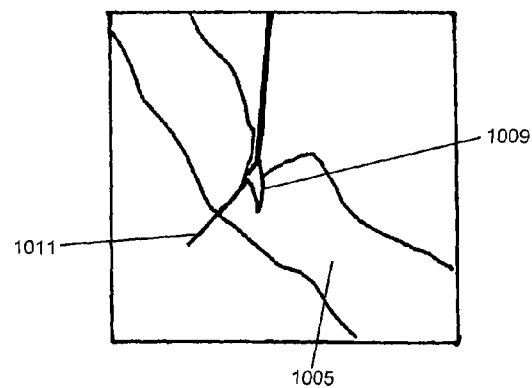

In one embodiment, as shown in FIGS. 10C and 10D, a tool (1009) may be used to issue commands inside the workspace. For example, the cutting tool (1009) may be used to define a planned incision line (1010) by tracing the cutting tool (1009) over tissue (1005) and along a desired cutting path. The robot may then take into account additional sensory information to adjust and to follow the incision line (1011) to cut tissue (1005), as shown in FIG. 10D. In one embodiment, the sensory information may be obtained via optical, force and/or position sensors of the robot. In one embodiment, a controller may be directly or indirectly attached to the tool (1009). The controller may receive surgeon interaction inputs, including tracing performed via the tool (1009), which may be used to define the planned incision line (1010).

In one embodiment, the surgeon interaction inputs may include tracing or drawing on the workspace with the tool (1009), where the tool (1009) may be attached to the controller, and the tracing or drawing defines parameters of tissue cutting or tissue dissection to be performed by the robot. The robot may then perform the tissue cutting or tissue dissection in an automated manner, taking into account sensor information. In one embodiment, tissue joining, including tissue suturing or clipping methods that may be defined using surgeon interaction inputs. The surgeon interaction input may include selecting an area of workspace using the controller to indicate an area of tissue to be joined. The robot may then perform the tissue joining in an automated manner, taking into account sensor information.

In one embodiment, a workspace display may be provided to depict the incision line (1010) being traced by the cutting tool (1009). In one embodiment, the workspace display may be a LCD display screen or a touchscreen panel. In one embodiment, the workspace display may be an image projection that is projected directly on a patient or to a suitable location in the operating location. In one embodiment, the workspace may include at least partially an endoscopic view.

By defining a planned incision line (1010), a cut may be performed by the robot in an automated or semi-autonomous manner. In one embodiment, an automated or semi-autonomous cut may be desired in the event a surgeon is fatigued, or if high dexterity or repetition is desired for the cut, for example. In one embodiment, the controller of the robot may receive the planned incision line (1010) and the sensory information in order execute commands to direct the cutting tool (1009), via a robot arm, to properly cut the tissue (1005).

Figure 10E:
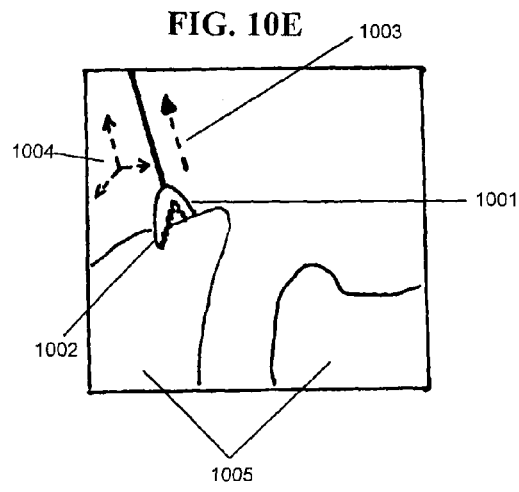
FIGS. 10E and 10F show an example of collaborative actions between a robot and a surgeon where a surgeon may define a planned position or a planned force vector.
Figure 10F:
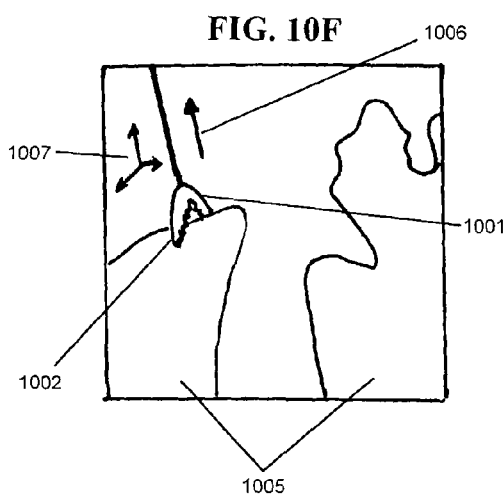

In one embodiment, as shown in FIGS. 10E and 10F, a robot may assist in the grasping of tissue in a collaborative manner. The surgeon may use a grasper (1002) to hold tissue (1005) in place. The surgeon may then issue a command, or signal to the robot, to define either a planned position (1004) or a planned force vector (1003). The robot may then hold this position (1007) or constant force (1006), based on the planned position (1004) or planned force vector (1003), respectively. In one embodiment, a force sensor (1001) may be provided to detect forces asserted at a tool tip when the surgeon issues the command to define the planned force vector (1003). In one embodiment, both a planned position (1004) and a planned force vector (1003) may be used. The combination of position and/or force information allows the robot to collaborate with the surgeon and to accomplish tasks for which each is well-suited. By allowing the robot to hold a position, the surgeon may be freed from having to continually assert force to maintain the holding position.

Figure 11:
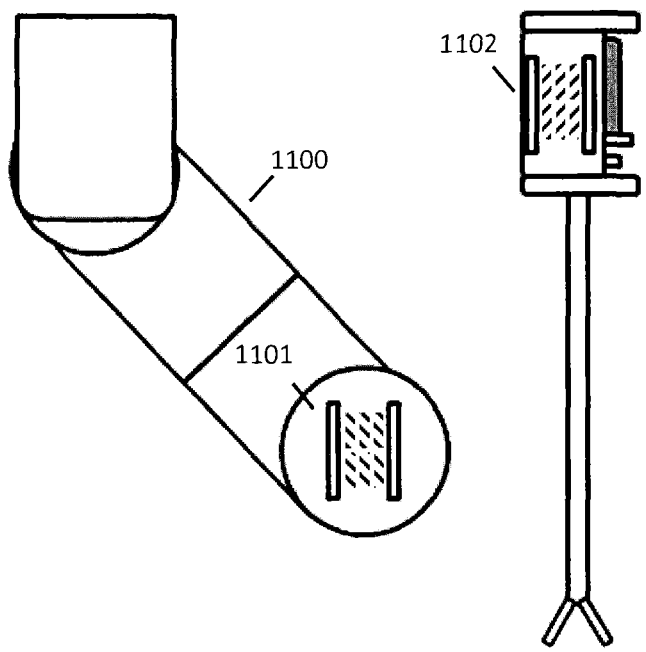
FIG. 11 shows an example of a universal tool port on a robot.
Figure 12:
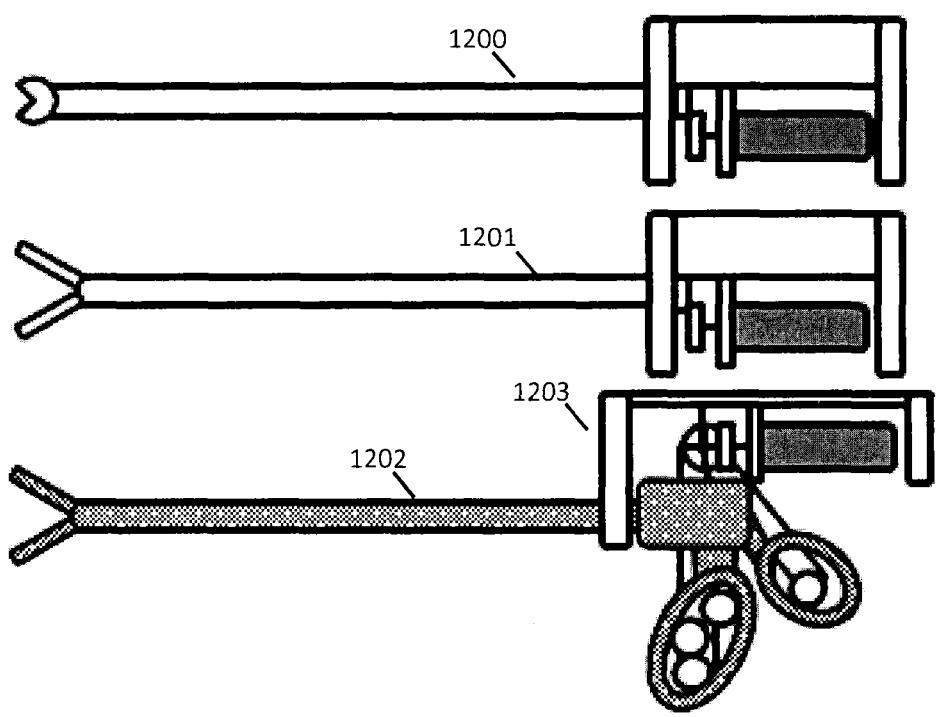
FIG. 12 shows examples of tools that may be attached to a robot.

In one embodiment as shown in FIG. 11, a robot (1100) with a tool port (1101) may be used to interface with and control a variety of surgical tools (1102). The tool port (1101) of the robot (1100) may include one or more mechanical and/or electrical contacts for transmitting power or data. FIG. 12 shows different types of tools the robot may interface with. The tool may be a specialized tool (1200) meant for use in autonomous routines (e.g. a tool optimized for suturing in autonomous anastomosis), a version of a standard laparoscopic tool built (1201) to interface with the robot (e.g. a motorized grasper or scalpel), or a manual laparoscopic tool (1202) attached to a universal tool adapter (1203) that is used to actuate the tool. The tool may have a range of actuations and degree of freedoms, and does not necessarily have to utilize all mechanical or electrical contacts that may be available on the robot.

To facilitate a collaborative hybrid surgical approach, a universal tool adapter may be mounted to the tool port of the robot that enables easy transition from manual to master-slave and autonomous procedures. The tool adapter may be designed to accommodate any number of different laparoscopic hand tools, and provides a platform capable of mechanizing the degrees of freedom and end effector actuation. In one embodiment, FIG. 1 illustrates a surgeon performing either manual or teleoperated laparoscopic surgery with a universal tool adapter (110). By placing the hand inside of the adapter (110), the surgeon can access the handle and articulation rings of a manual tool while under intelligent support from the robotic arm (100). If mechanized control is needed, the surgeon may remove their hands from the manual tool and connect the tool to the tool adapter. In one embodiment, controls located directly on the tool adapter may be provided to allow the surgeon to teleoperate the robot while still maintaining arm support. The universal tool adapter (110) may be equipped with force and torque sensors to provide feedback for the teaching of no fly-zones, tool memory, and/or path planning with the collaborative hybrid approach.

Figure 13:
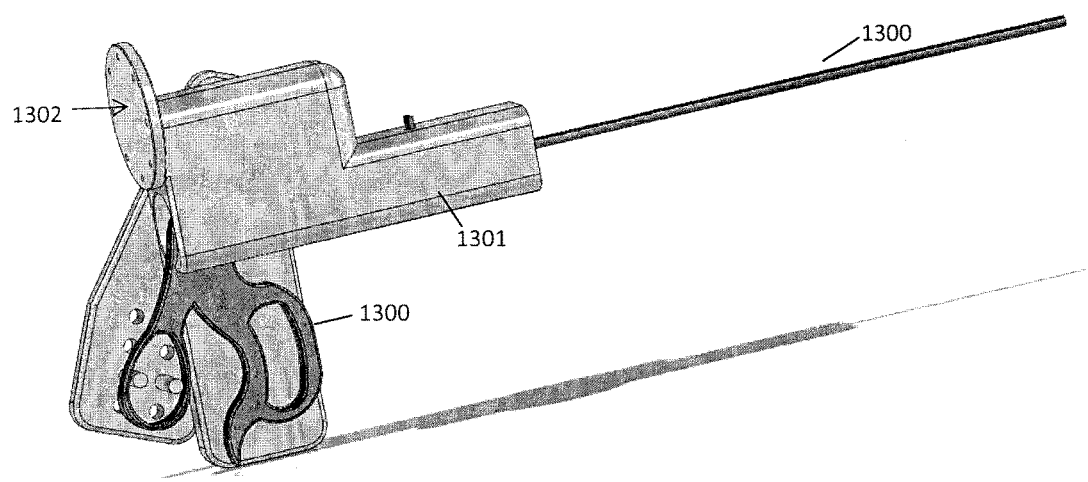
FIGS. 13-15 show an embodiment of the present disclosure as a universal tool adapter.
Figure 14:
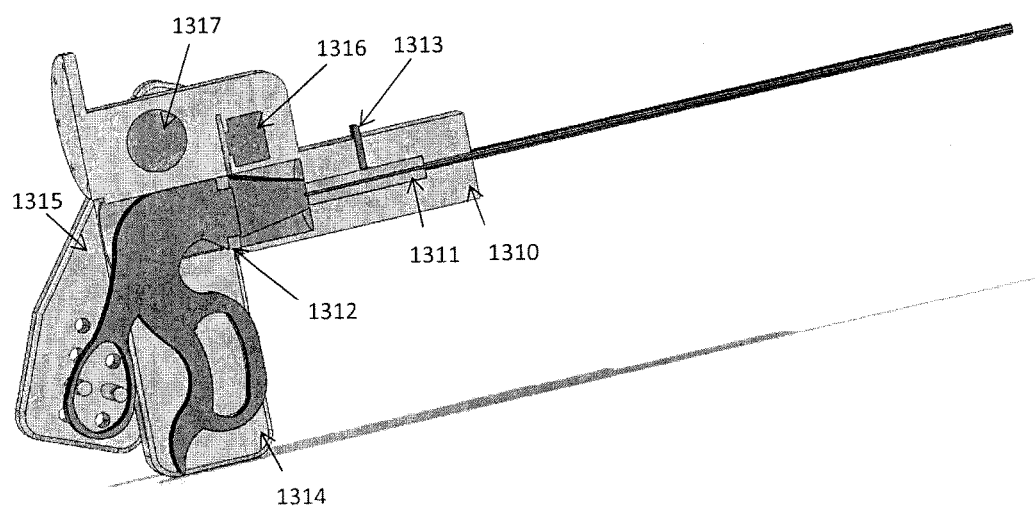
Figure 15:
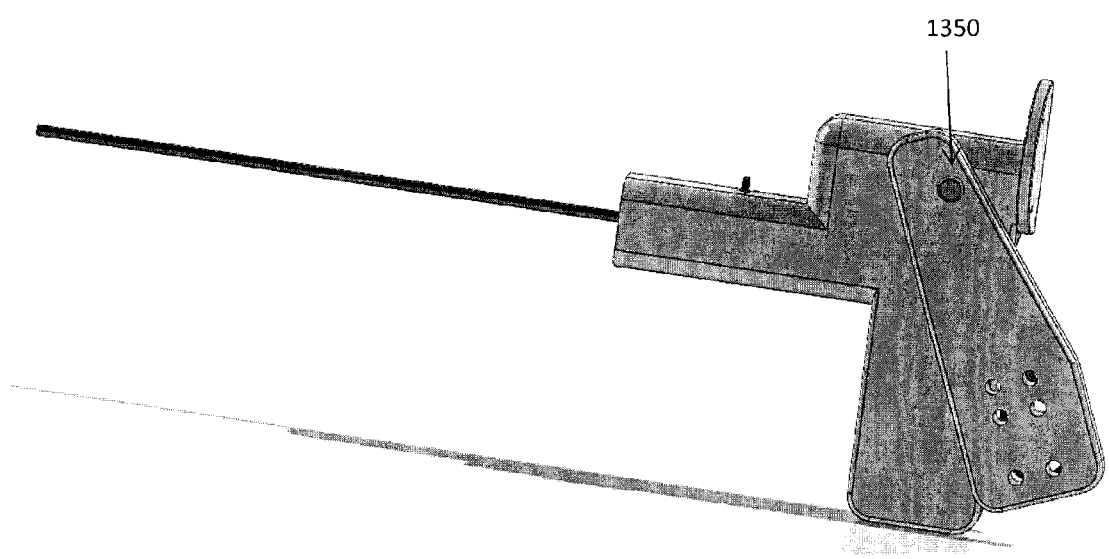

In one embodiment, FIGS. 13-15 show an exemplary universal adapter for tools (1300) that provide one degree of freedom for rotation and one for operation, e.g. cutting, or clamping such as graspers, needle drivers, and scissors. A tool (1300) of this type may consist of a shaft with standardized diameter, a rotating ring to rotate the shaft, a stationary handle, and a moving handle that activates an action at the shaft tip, i.e. clamping or scissor actuation. Size and position of the handles may vary between different tools, so a universal adapter needs to be able to be configured to adjust to the specific size and motorization needs of the tool. In one embodiment, the tools (1300) may include a manual surgical tool and/or a robotic surgical tool. In one embodiment, the tools (1300) may include laparoscopic tools and/or an electrocautery tool. In one embodiment, the tools (1300) may include non-modular surgical tools. In one embodiment, the tools (1300) may include modular surgical tools.

In one embodiment, the tool (1300) may be inserted into the adapter (1301), by placing it into a revolver sleeve (1310), consisting of a cylindrical sleeve (1311) made of two halves that clamp together, a spring clamp (1312) that engages a rotary feature of the tool (1300), and a thumb screw (1313). The cylindrical opening of the sleeve (1310) is designed to have a smaller diameter compared to the tool, to provide adequate clamping force on the tool. The revolver sleeve (1310) may be exchanged to adjust for the specific standardized diameter of the tool (1300). The revolver sleeve (1310) aligns the tool (1300) concentrically with an axis of rotation of the revolver sleeve (1310). Before locking the tool (1300) in position with the thumb screw (1313), the spring clamp (1312) pushes the tool axially forward until the shoulder of the rotary feature of the tool rests against the end of the revolver sleeve (1310), setting the tool (1300) into a repeatable axial and rotational position.

In one embodiment, the adapter (1301) may comprise a stationary member (1314) and a moving member (1315) that rotates about a hinge point (1350). The moving member (1315) may contain an array of pin holes. In one embodiment, the array of pin holes may include a plurality of rows and columns of pin holes on the moving member (1315). By securing at least one mounting pin onto the moving member (1315) via the pin holes such that the pins are inside a moving handle of the tool (1300), the pins may engage the sides of the moving handle. In one embodiment, the moving member (1315) may be provided with at least two mounting pins secured to the pin holes of the moving member (1315). The at least two pins may interact with an inside portion of the moving handle. In one embodiment the at least two mounting pins may engage a movable portion of the tool (1300) while the stationary member (1314) may engage a fixed portion of the tool (1300). In one embodiment, the tool (1300) may be a laparoscopic tool.

By adjusting pin positions, the adapter (1301) can accommodate multiple tool sizes and tool shapes. Once the tool (1300) is positioned into the adapter (1301), two motors (1316, 1317) may actuate the rotational degree of freedom and the other operation, e.g. cutting or clamping. Alternatively, the rotational degree of freedom may be implemented with the robotic arm. In one embodiment, the adapter (1301) may include a flange (1302) to detachably attach the adapter (1301) to a robotic arm of the present disclosure. In one embodiment, the adapter (1301) is configured to quickly and easily attach to or detach from the robotic arm. In one embodiment, at least one of the two motors (1316, 1317) may be mounted to the stationary member (1314), the at least one of the two motors (1316, 1317) being connectable with a rotational portion of the tool (1300) to drive the tool (1300).

Figure 16:
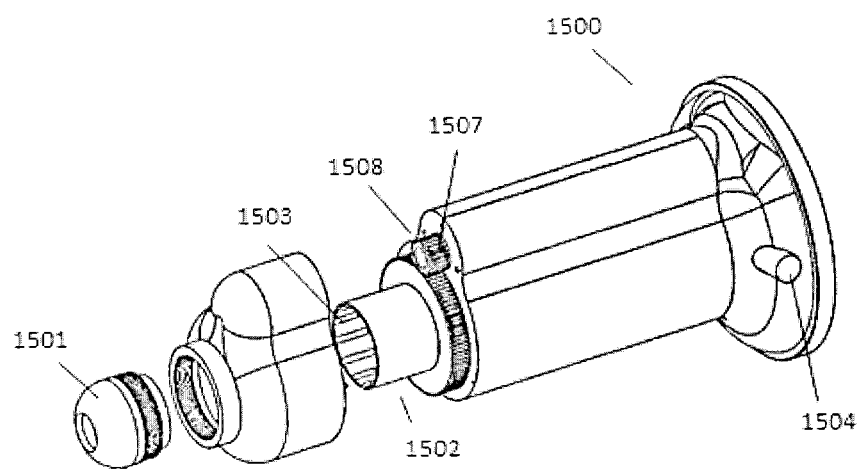
FIG. 16 shows an example of a universal tool adapter for modular tools.
Figure 17:
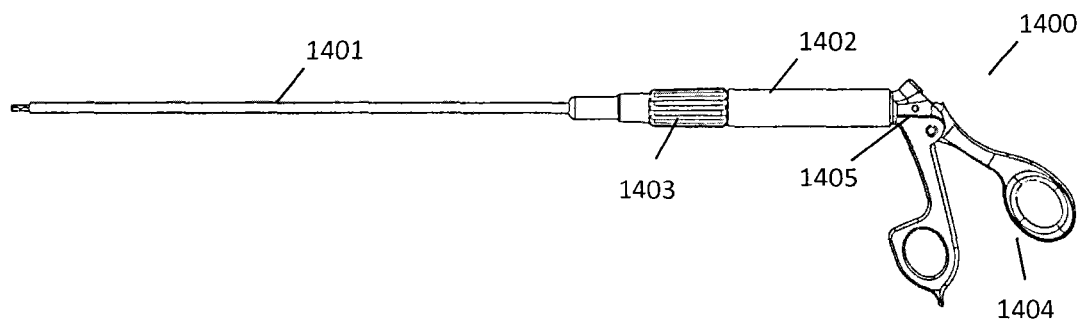
FIG. 17 shows an example of a modular multi degree of freedom tool.

In one embodiment, FIG. 16 shows an exemplary universal tool adapter (1500) for modular multi degree of freedom tools. FIG. 17 illustrates the features of a modular tool (1400). Tools of this type may comprise of a shaft (1401) with a standardized diameter, a rotating ring (1402) to rotate the end effector, an articulation collar (1403) that controls bending of the tool tip when rotated, a moving handle (1404) that actuates the function of the end effector, i.e. grasping or cutting, and a quick connect interface (1405) to engage and disengage the end effector from the handle. Because modular tools have similar end effector geometry and quick connect interfaces, the universal tool adapter can accommodate a complete modular tool set. Additionally, multiple axes are provided to control for single and multi degree of freedom tools.

Figure 18:
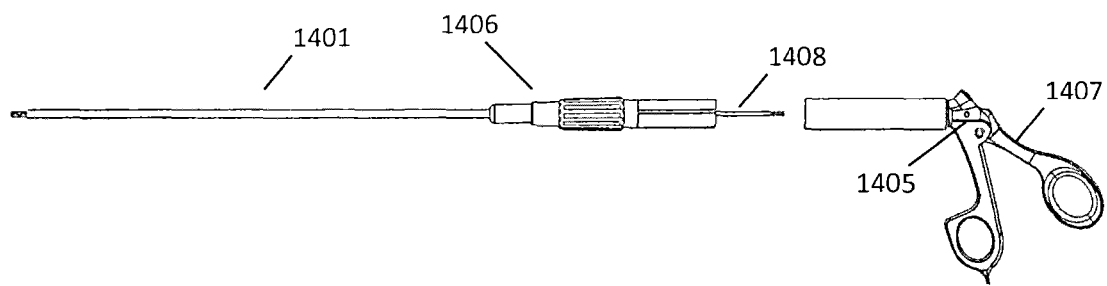
FIG. 18 shows an example of a modular hand tool with an end effector disengaged from the handle.

In one embodiment, the end effector (1406) may be disengaged from the modular handle (1407) of a modular tool (1400) by manipulating the quick connect interface (1405) as shown in FIG. 18. A cap (1501) of the universal tool adapter (1500) may be removed to expose an articulation interface (1502), where the modular end effector (1406) may be seated inside of the universal tool adapter (1500). The articulation interface (1502) may include ridges (1503) that align with corresponding grooves of the articulation collar (1403) for tool orientation, and torque transmission. Once seated, the modular end effector (1406) may be secured within the tool adapter (1500) by replacing and fastening the threaded cap (1501). In one embodiment, the modular tool (1400) may be secured to the tool adapter (1500) via at least one of pins, springs, or threaded portions. In one embodiment, the modular tool (1400) may be a laparoscopic tool.

Figure 19:
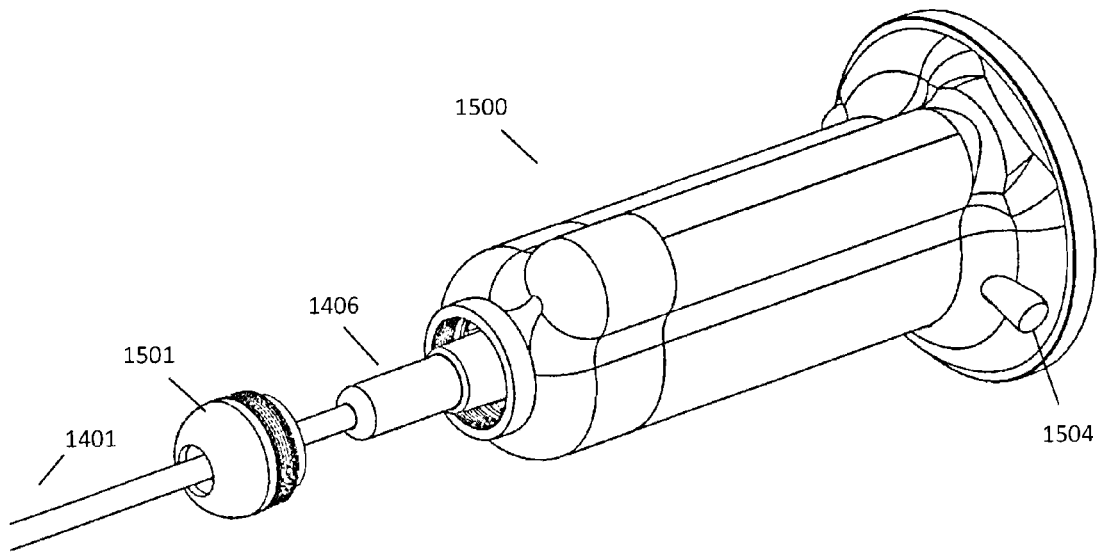
FIG. 19 shows an example of an end effector being installed onto the universal tool adapter.
Figure 20:
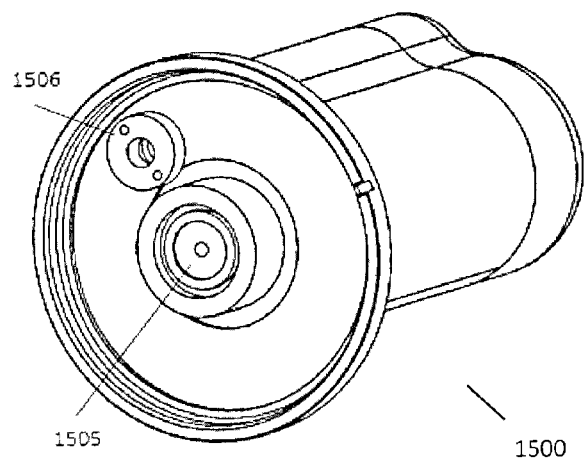
FIG. 20 shows an example of the universal tool adapter including a motor pack interface.

In one embodiment, a quick connect button (1504) may be depressed once the modular end effector (1406) has been seated to engage a spring loaded linear drive interface (1505) shown in FIGS. 19 and 20. The universal tool adapter (1500) may include a drive interface (1505) actuatable to translate along an axial direction of the tool adapter (1500) in order to control a function of the end effector, ie. grasping and cutting.

In one embodiment, actuation of the modular end effector (1409) may be achieved by moving a translational stage that pushes actuation drive shaft (1408) of the modular end effector (1406) forward, opening the jaws of the modular end effector (1409). As the drive shaft is pushed, an internal spring is compressed putting pressure on the linear drive interface (1505). When the push is reversed, the compressed spring is able to relax, returning the actuation drive shaft (1408) to a home state and closing the jaws of the modular end effector (1409). This action may be repeated for actuating the end effector of any modular tool.

Figure 21:
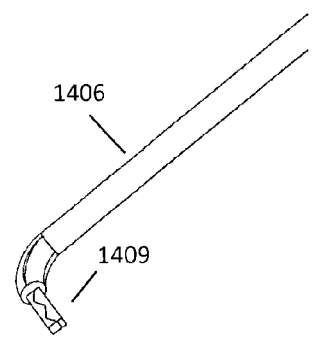
FIG. 21 shows an example of a modular end effector that may be articulated via a motor of the motor pack.

In one embodiment, articulation of the modular end effector (1406) may be achieved by rotating an articulation rotor (1506), which may then transmit torque to an intermediate gear (1507) via a drive shaft (1508). The intermediate gear (1507) may engage and rotate the articulation interface (1502) of the universal tool adapter (1500), and hence rotation of the articulation collar (1403) of the modular end effector (1406). As the articulation collar (1403) is rotated, an end effector (1409) may be bent between 0 and 90° as shown in FIG. 21.

Figure 22:
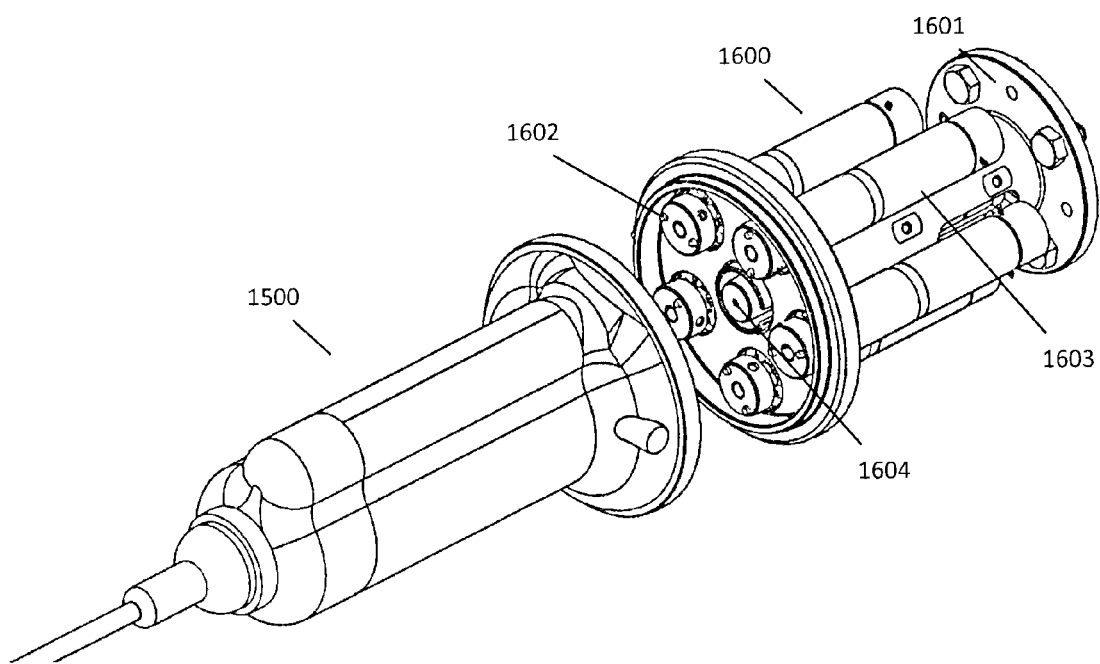
FIG. 22 shows an example of a multi axis motor pack being mounted to the universal tool adapter.

In one embodiment, as shown in FIG. 22, a multi axis motor pack (1600) may be mounted to the universal tool adapter (1500) to mechanize a tool. The motor pack (1600) may be mounted on a robotic positioning system via a mounting flange (1601). In one embodiment, spring loaded pins (1602) may be provided on at least one rotational motor (1603) to engage an articulation rotor (1506) on the universal tool adapter (1500). At least one rotational motor (1603) may be rotated to transmit a rotational force to the articulation rotor (1506). At least one linear motor (1604) may be used to transmit axial force to the drive interface (1505).

In one embodiment, the multi axis motor pack (1600) may include a plurality of rotational motors (1603) and/or a plurality of linear motors (1604). In one embodiment, the multi axis motor pack (1600) may include plurality of rotational motors (1603) arranged symmetrically about a central axis of the motor pack (1600). In one embodiment, a linear motor (1604) may be disposed along the central axis of the motor pack (1600). By providing a multi axis motor pack (1600) with a plurality of rotational motors (1603) and/or a plurality of linear motors (1604), the multi axis motor pack (1600) may be compatible with any number of universal tool adapters having multiple articulation rotors and/or multiple linear drive interfaces, which in turn may be used to drive modular end effectors with multiple degrees of freedom.

The specific embodiments described above have been shown by way of example in a surgical case and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

As used herein, the terms "comprises," "comprising," "including," and "includes" are to be construed as being inclusive and open-ended. Specifically, when used in this document, the terms "comprises," "comprising," "including," "includes," and variations thereof, mean the specified features, steps or components included in the described features of the present disclosure. These terms are not to be interpreted to exclude the presence of other features, steps or components.

It is understood that the hybrid control surgical robotic system of the present disclosure is not limited to the particular embodiments disclosed herein, but embraces much modified forms thereof that are within the scope of the following claims.

The invention claimed is:
1. A surgical robotic system, comprising:
at least one robot arm;
at least one sensor to detect an input or an operating condition of the at least one robot arm;
a first control circuitry configured to detect surgeon interaction input, the first control circuitry being detachably attached to the at least one robot arm; and a second control circuitry configured to process the input or the operating condition and/or the surgeon interaction input, and to operate the at least one robot arm in a plurality of operating modes,
  wherein the second control circuitry executes commands to the at least one robot arm to share a workspace and surgical elements.

2. The surgical robotic system of claim 1, wherein the surgical elements include at least one of a manual surgical tool, a robotic surgical tool, an electrocautery tool, and a display of the workspace.

3. The surgical robotic system of claim 2, further comprising:
  a surgical tool adapter,
  wherein the manual surgical tool or the robotic surgical tool is attachable to and detachable from the surgical tool adapter to provide at least one degree of actuation for tool operation of the manual surgical tool or the robotic surgical tool, and
  wherein the surgical tool adapter is controllable via the at least one robot arm or by manual operation.

4. The surgical robotic system of claim 3,
  wherein the manual surgical tool is a non-modular surgical tool,
  wherein the surgical tool adapter includes a stationary member and a movable member secured to the non-modular surgical tool, and
  wherein the movable member comprises a plurality of pin holes and at least two mounting pins, the at least two mounting pins being rearrangeable on the plurality of pin holes to engage a movable portion of the non-modular surgical tool with the movable member.

5. The surgical robotic system of claim 3, wherein the manual surgical tool or the robotic surgical tool is a modular surgical tool,
  wherein the modular surgical tool is drivingly secured to the surgical tool adapter via a linear drive interface, an articulation rotor, or a gear, and
  wherein the linear drive interface, the articulation rotor, or the gear is driven by a rotational motor or a linear rotor interfaced with the surgical tool adapter.

6. The surgical robotic system of claim 3, wherein the surgical tool adapter includes a motor pack having at least one rotational motor or linear motor, the motor pack being drivingly connected to the robotic surgical tool, and the robotic surgical tool being detachably coupled to the tool adapter via at least one of pins, springs, or threaded portions.

7. The surgical robotic system of claim 2, wherein the display of the workspace includes at least partially an endoscopic view.

8. The surgical robotic system of claim 1,
  wherein the at least one sensor is a force sensor or a position encoder coupled to the at least one robot arm, and
  wherein the force sensor or the position encoder detects the surgeon interaction input from the first control circuitry.

9. The surgical robotic system of claim 8,
  wherein the second control circuitry generates a kinematic model of a surgeon based on the surgeon interaction input from the first control circuitry in a calibration step, and
  wherein the second control circuitry operates the at least one robot arm based on the kinematic model to provide dynamic support in order to reduce surgeon fatigue.

10. The surgical robotic system of claim 9, wherein the calibration step includes receiving surgeon interaction inputs from the first control circuitry based on one or more detected arm positions in the shared workspace by the at least one sensor and based on force sensed by the at least one sensor to generate the kinematic model.

11. The surgical robotic system of claim 9,
  wherein the at least one robot arm provides the dynamic support as a dynamic force by asserting a counter force to an external force applied to the at least one robot arm, and
  wherein the external force includes at least a gravitational force applied by a surgical tool attached to the at least one robot arm.

12. The surgical robotic system of claim 1,
  wherein the plurality of operating modes comprises a fully automated mode and a partially automated mode, and
  wherein the second control circuitry operates the at least one robot arm in the fully automated mode or the partially automated mode based on the surgeon interaction input from the first control circuitry and/or sensory information for the at least one sensor.

13. The surgical robotic system of claim 12,
  wherein the surgeon interaction input may include movement or force sensed by the at least one sensor,
  wherein the at least one sensor includes a force sensor and a position sensor, and
  wherein the second control circuitry operates the at least one robot arm to perform at least one of defining no-fly zones, tissue grasping, tissue cutting, tissue dissection, tissue joining, and tissue retraction based on the surgeon interaction input.

14. The surgical robotic system of claim 13, wherein the surgeon interaction input defines a planned position or a force vector in the shared workspace for the at least one robot arm to execute or maintain.

15. The surgical robotic system of claim 13,
  wherein the surgeon interaction input defines at least one no-fly zone, the at least one no-fly zone being a conventional volumetric zone or a task-specific zone having abstract geometries including planes, and
  wherein the surgeon interaction input includes a trace of a boundary from the first control circuitry.

16. The surgical robotic system of claim 13,
  wherein the surgeon interaction input defines the tissue cutting or the tissue dissection performed by the at least one robot arm, and
  wherein the surgeon interaction input includes a trace or a drawing on the workspace from the first control circuitry with a surgical tool attached.

17. The surgical robotic system of claim 13,
  wherein the surgeon interaction input defines the tissue joining, including tissue suturing or clipping methods, and
  wherein the surgeon interaction input includes a trace or a selection of an area of the workspace from the first control circuitry to indicate an area of tissue to be joined.

18. The surgical robotic system of claim 13, wherein the second control circuitry executes a command to provide haptic feedback.

19. The surgical robotic system of claim 12, wherein automated operations during the fully automated mode or during the partially automated mode are interrupted or adjusted due to a subsequent surgeon interaction input from the first control circuitry.

* * * * *